(12) United States Patent
Mahrenholz et al.

(10) Patent No.: US 11,478,292 B2
(45) Date of Patent: Oct. 25, 2022

(54) DEVICE FOR GENERATING A COLD ATMOSPHERIC PRESSURE PLASMA

(71) Applicant: Leibniz-Institut für Plasmaforschung und Technologie e.V., Greifswald (DE)

(72) Inventors: Carsten Mahrenholz, Berlin (DE); Tobias Gura, Eggesin (DE); Rene Bussiahn, Greifswald (DE); Stephan Krafczyk, Greifswald (DE); Manfred Stieber, Greifswald (DE); Stefan Horn, Loissin (DE); Ronny Brandenburg, Grob Kiesow OT Kessin (DE); Klaus-Dieter Weltmann, Binz (DE); Thomas Von Woedtke, Sundhagen (DE)

(73) Assignee: LEIBNIZ-INSTITUT FÜR PLASMAFORSCHUNG UND TECHNOLOGIE E.V., Greifswald (DE)

(*) Notice: Subject to any disclaimer, the term of this patent is extended or adjusted under 35 U.S.C. 154(b) by 990 days.

(21) Appl. No.: 15/517,956

(22) PCT Filed: Oct. 9, 2015

(86) PCT No.: PCT/EP2015/073484
§ 371 (c)(1),
(2) Date: Apr. 9, 2017

(87) PCT Pub. No.: WO2016/055654
PCT Pub. Date: Apr. 14, 2016

(65) Prior Publication Data
US 2017/0231680 A1    Aug. 17, 2017

(30) Foreign Application Priority Data
Oct. 9, 2014   (DE) .......................... 102014220488.7

(51) Int. Cl.
*A61B 18/04*     (2006.01)
*H05H 1/24*      (2006.01)
(Continued)

(52) U.S. Cl.
CPC .......... *A61B 18/042* (2013.01); *A61B 18/085* (2013.01); *A61B 18/10* (2013.01);
(Continued)

(58) Field of Classification Search
CPC ....... A61B 5/04; A61B 18/042; A61B 18/085; A61B 18/10; A61B 2018/22853;
(Continued)

(56) References Cited

U.S. PATENT DOCUMENTS 9,330,890 B2 * 5/2016 Busse ...................... A61N 1/40
2006/0042545 A1 * 3/2006 Shibata ............. H01J 37/32009
118/722

(Continued)

FOREIGN PATENT DOCUMENTS

CN   102711909 A   10/2012
DE   10136403      2/2003
(Continued)

OTHER PUBLICATIONS

Biennial Report 2012/2013, Leibniz Institute for Plasma Science and Technology. Plasma-FlUssigkeits-Wechselwirkungen, vorgelegt von, Katrin Oehmigen, geboren am Mar. 12, 1982, in Greifswald, Greifswald, Sep. 2013.
(Continued)

*Primary Examiner* — Thomas A Giuliani
*Assistant Examiner* — Christine A Dedoulis
(74) *Attorney, Agent, or Firm* — Soroker Agmon Nordman (57) ABSTRACT

The invention relates to a device for producing a cold atmospheric pressure plasma for the treatment of human
(Continued)

and/or animal surfaces, comprising a flexible, planar multilayer system with a side facing the surface to be treated and a side facing away from the surface to be treated, wherein the multilayer system comprises the following layers, namely a first electrode layer on the facing away side of the multilayer system, second electrode layer on the facing side of the multilayer system, wherein the electrode layer has a plurality of recesses or is formed in a grid-like or meander-shaped fashion, a dielectric layer arranged between the first electrode layer and the second electrode layer, and a spacer layer arranged adjacent the second electrode layer on the facing side of the multilayer system. In addition, the invention relates to a cable, a generator unit for providing a high voltage, and a system.

16 Claims, 5 Drawing Sheets

(51) Int. Cl.
*A61B 18/08* (2006.01)
*A61B 18/10* (2006.01)
*A61N 1/44* (2006.01)

(52) U.S. Cl.
CPC ............ *A61N 1/44* (2013.01); *H05H 1/2406* (2013.01); *H05H 2277/10* (2013.01)

(58) Field of Classification Search
CPC ............ A61B 3/0066; A61B 5/150763; A61B 5/150786; A61B 19/44; A61B 90/90; H05H 1/2406; H05H 2001/2412; H05H 2277/10; A61C 2204/005
See application file for complete search history.

(56) References Cited

U.S. PATENT DOCUMENTS

| | | | |
|---|---|---|---|
| 2006/0133970 A1* | 6/2006 | Imanishi | B01D 53/92 422/186 |
| 2006/0200122 A1* | 9/2006 | Sartor | A61B 18/042 606/41 |
| 2011/0137306 A1* | 6/2011 | Allen | A61B 90/90 606/41 |
| 2012/0046602 A1* | 2/2012 | Morfill | A61L 2/0011 604/23 |
| 2012/0271225 A1* | 10/2012 | Stieber | A61B 18/042 604/26 |
| 2013/0345620 A1* | 12/2013 | Zemel | A61B 18/042 604/24 |
| 2014/0182879 A1 | 7/2014 | Busse | |
| 2015/0343231 A1* | 12/2015 | Sanders | A61B 18/042 607/2 |

FOREIGN PATENT DOCUMENTS

| | | | |
|---|---|---|---|
| DE | 102008030913 | 1/2010 | |
| DE | 10 2011 001 416 A1 | 9/2012 | |
| DE | 10 2009 060 627 B4 | 6/2014 | |
| EP | 2170022 | 3/2010 | |
| EP | 2323600 B1 * | 2/2014 | ....... A61F 13/00051 |
| WO | 2007067924 | 6/2007 | |
| WO | 2014040630 | 3/2014 | |

OTHER PUBLICATIONS

Institute Leibniz: "Biennal Report 2012/2013", Jan. 1, 2014.

* cited by examiner

DEVICE FOR GENERATING A COLD ATMOSPHERIC PRESSURE PLASMA

RELATED APPLICATIONS

The present application claims priority as a US national phase under 35 U.S.C. 363 of PCT/EP2015/073484 filed on Oct. 9, 2015, the disclosure of which is incorporated herein by reference.

The invention relates to a device for generating a cold atmospheric pressure plasma for the treatment of human and/or animal surfaces according to claim 1, a cable according to claim 12, a generator unit for providing a high-voltage according to claim 14, and a system according to claim 16.

In plasma medicine, promising applications in the treatment of living tissue have been developed in the last few years, from the collaboration of classical plasma-physics and life sciences. The focus of the plasma applications was on the use of non-thermal atmospheric pressure plasmas for decontamination up to the sterilization of living tissue, i.e. the killing of pathogens on or in a living tissue. However, the plasma treatment is not limited to disinfection and sterilization. Other applications which exploit the particular properties of the plasma can also have beneficial effects for the medicine.

A possible use of plasma is the promotion of healing of wounds, such as chronic and/or postoperative wounds, but also the treatment of burns, abrasions, eye and mucous membrane infections, etc. In addition, also the use for disinfection, wrinkle treatment and/or other cosmetic treatments can be envisioned. In particular chronic wounds, such as diabetes-induced wounds, cause a great suffering in the affected patients and are often associated with high stress for the patient. Conventional therapy approaches in many cases do not lead to the desired healing of the wounds, so that often only the status quo is maintained.

A promising approach to therapy of chronic wounds is the use of cold plasmas, so-called atmospheric pressure plasmas. Plasma is considered a fourth state of matter and consists of ionized gas with physical peculiarities. Plasma is electrically charged gas and conducts electrical current. In addition, it contains a variety of radicals, such as free electrons, ions, and/or other excited species. Furthermore, plasma emits UV and visible light as well as other electromagnetic fields.

By the development of body-compatible plasmas with temperatures of less than 40° C. a new, highly actual research field emerged—the plasma medicine. These "cold plasmas" are the basis of many different applications in plasma medicine. Known, available plasma sources have demonstrated their ability in the context of the therapy of various skin diseases and/or the treatment of chronic wounds in clinical trials. A substantial disadvantage of the known plasma sources, however, is that until now only small wound areas can be treated since the known plasma sources are relatively small. Moreover, known plasma sources are difficult to control, i.e., difficult to dose and handle.

There is therefore a need for an improved, large-area plasma source for atmospheric pressure plasmas, particularly for the treatment of human and/or animal surfaces.

The object of the present invention is to provide a device for producing a cold atmospheric pressure plasma for the treatment of human and/or animal surfaces, wherein a large-area, in particular approximately 400 $cm^2$, plasma source is to be provided. In addition, the plasma source is to adapt flexibly to the topography of the surfaces to be treated, particularly to the different sizes and shapes of the application area and the application. It is also an object of the invention to provide a cable, a generator and a system for operating a (plasma) device for producing a large-area, cold atmospheric pressure plasma for the treatment of human and/or animal surfaces.

The above object is achieved according to the invention by an apparatus for producing a cold atmospheric pressure plasma for the treatment of human and/or animal surfaces according to claim 1, a cable according to claim 12, a generator unit for providing a high-voltage as claimed in claim 14 and a system according to claim 16. Subject matter according to the dependent subclaims describe preferred embodiments of the invention.

A first aspect of the invention relates to a device, in particular a plasma device, for producing a cold atmospheric pressure plasma for the treatment of human and/or animal surfaces, comprising a flexible, planar multilayer system with a side facing the surface to be treated and a side facing away from the surface to be treated, wherein the multilayer system comprises the following layers, namely a first electrode layer on the facing away side of the multilayer system, a second electrode layer on the facing side of the multilayer system, wherein the electrode layer has a plurality of recesses or is formed as a grid or meandering, a dielectric layer which is arranged between the first electrode layer and the second electrode layer, and at least one spacer or a spacer layer adjacent to the second electrode layer on the facing side of the multilayer system.

In the following, the concept of the invention is described by way of example without limiting the invention. The device according to the invention, in particular the plasma device, essentially serves for the treatment of human and/or animal surfaces, in particular the treatment of wounds, such as, for example, chronic and/or postoperative wounds. In addition, it is also used for the treatment of burns, abrasions, eye and mucous membrane infections, etc. The use for disinfection, wrinkle treatment and/or other cosmetic treatments is also conceivable.

The device makes use of a special, flexible (possibly elastic) electrode arrangement with at least two electrode layers, namely a high-voltage electrode and a ground electrode, for generating an extensive plasma, in particular a cold atmospheric pressure plasma, with the aid of a dielectric layer between the two electrodes. The device according to the invention is thereby configured to adapt flexibly, in particular positively, to arbitrarily curved surfaces, for example in the face of a patient, and thus also to make—for known and inflexible plasma sources—inaccessible skin regions, such as, for example, the fingers or toes accessible for a plasma treatment. The device produces an extensive plasma on one side of the device and is then placed with this side on the surface to be treated, in particular on the wound, so that the advantageous effects/properties of the plasma can act on the surface or interact with it.

According to the invention, at least four layers are provided for the provision of a flexible, large-area, dielectric barrier surface discharge: two or three flexible electrodes, namely a first and a second electrode layer in a respective electrode plane, e.g. copper foils or other conductive materials, a flexible and/or non-flexible functional dielectric between the respective electrodes, e.g., silicone, Kapton, PVDF, ETFE, and a spacer layer.

The functional dielectric is preferably designed to be flexible. However, it is also possible to use non-flexible, but then flexibly interconnected, materials.

Preferably, but without limitation, a polymer is used.

In other exemplary embodiments, elastomers, textile fabrics or, for example, ceramics embedded in a silicone matrix or open-cell foams, such as, for example, chitin substances, such as chitosan or chitosan plasters, are used. In order to ignite the plasma, a high voltage is applied to one of the two electrodes, the second electrode then being at earth or ground potential and thus forming a counterelectrode for the high voltage electrode.

Between the two electrodes is then a high voltage field, wherein a short circuit in the form of an electric arc between the electrodes is prevented or prohibited by the dielectric layer. Instead, a large-area dielectric barrier atmospheric pressure plasma is formed.

Since the plasma properties depend strongly on the gas space thickness, in particular on the gas volume between the ground electrode and the surface to be treated, in particular on the skin, a spacer layer is provided which allows reliable and reproducible provision of a sufficient gas quantity for generating a plasma with defined plasma properties.

The gas to be ionized is either a working gas or mixed gas and/or the ambient or external air. Without limiting the invention, the spacer layer can be embodied in a variety of ways, for example with webs, recesses, knobs, foams of conventional wound dressings and/or conventional wound dressing, etc., which can then have different shapes and thicknesses. For example, the spacer layer can also be designed in the form of a self-adhesive margin, with which the device is attached to the patient. The electrodes are preferably formed with conductive materials, in particular with metals, for example in the form of thin metal layers, films, gratings and/or conductive polymer layers. These and further preferred embodiments of the invention are the subject matter of the subclaims and disclose in detail advantageous possibilities how the invention can be realized or designed in the context of the task as well as with regard to further advantages.

Preferably, according to one embodiment, the spacing support layer is formed with at least one polymer, in particular an elastomer, and/or a textile fabric, and with thicknesses of between 0.5 mm and 5 mm.

In a suitable embodiment, it may be provided that the multilayer system additionally has a first insulating layer, wherein the first insulating layer is arranged adjacent to the first electrode layer on that side of the multilayer system facing away from the surface to be treated. The first insulating layer is arranged on the side of the multilayer system facing away from the surface to be treated and, in a preferred embodiment, has a thickness of between 0.5 mm and 5 mm, preferably of 2 mm. The first insulating layer essentially serves for the electrical insulation of the first electrode layer, which is preferably designed as a high-voltage electrode layer, that is to say as an electrode layer on which a high voltage is applied. In a further development of this embodiment, the first electrode layer is insulated on several sides, in particular on all sides.

In an advantageous embodiment, it may be provided that the multilayer system additionally has a second insulating layer, the second insulating layer being arranged adjacent to the second electrode layer on that side of the multilayer system facing the surface to be treated. It is preferably provided that the second insulating layer has a thickness of between 10 μm and 300 μm.

A further embodiment may provide that the multilayer system additionally has a third insulating layer, the third insulating layer being arranged adjacent to the spacer layer on the side of the multilayer system facing the surface to be treated. Preferably, the insulating layer is formed with a skin- and/or wound-compatible material, preferably with antiseptic and/or atraumatic properties. In a further advantageous embodiment, the third insulating layer has a thickness of between 50 μm and 300 μm, preferably of 200 μm.

In one embodiment, the multi-layer system has dimensions that comprise a length and a width between 5 cm to 25 cm each.

A particularly advantageous embodiment relates to a multilayer system, wherein the first electrode layer is formed continuously or with a plurality of recesses.

In a suitable embodiment, provision may be made for the recesses in the first and/or the second electrode layer to have a hole-shaped, strip-shaped, meandering, honeycomb-shaped, circular and/or square design.

For example, the circular and/or honeycomb-shaped recesses can be formed as holes with a diameter of 3 mm to 5 mm, which are arranged in rows and/or staggered juxtaposed.

In another exemplary embodiment, square recesses with dimensions of 3 mm×3 mm to 5 mm×5 mm, preferably of 4 mm×4 mm are provided, wherein the webs between the recesses can have a width between 0.1 mm and 5 mm.

Again, in another embodiment strip-shaped recesses with a width between 1 mm and 10 mm, preferably with a width of 6 mm, are used. The strip-shaped recesses are then arranged, for example, parallel, circular, semicircular, helical and/or meandering.

A preferred embodiment provides that the device comprises an information carrier, for example a chip or a label or a label or another information and storage medium, on which operating parameters for operating the device are stored.

In particular in the case of a multiple use of the device, it is advantageous that the device-specific data, in particular the operating parameters for operating the device, are stored or saved on or at the device in an information storage and storage medium, for example a microchip, such that they can be read prior and/or during the operation of the device.

Possible data which are preferably stored can be data regarding a treatment scheme, the application duration, lifetime, pulse pattern, intensity (amplitude of the supply voltage), an ID or serial number of the device, the number of previous applications, hygienic status, (non-sterile, used, disinfected, sterile, etc.), errors or error messages during use of the device (e.g. breakdowns or short circuits, operating parameter fluctuations), usability/usage status (e.g. valid or invalid).

The reading of the information carrier or storage medium can be effected, for example, by cable, optically or by means of radio technology. In addition, a security element is also provided with such an information carrier, which, for example, releases operation of the device only if the necessary prerequisites are met. Also, with the help of the information carrier, multiple uses of a device can be prevented, for example, if a device may only be used once for hygienic reasons. A barcode or QR code solution is preferred for such a one-way device for reasons of cost. In this case, for example, the treatment parameters (operating parameters and a permissible indication) would have to be coded so that, for example, the authenticity (originality) of the device can be checked. This functionality can be implemented, for example, by means of an encrypted number circuit.

A second aspect of the invention relates to a cable for connecting to a device according to the first aspect of the invention, the cable having a connector configured to provide a pluggable high voltage connection between the device and the cable.

The cable serves, on the one hand, to supply the (plasma) device according to the first aspect of the invention with high voltage; on the other hand, the cable is preferably also designed to transmit control-technical signals between a supply unit and the device. The signals are to be transmitted bidirectionally, for example, from the plasma device to a supply/control unit and vice versa.

The essential task of the cable is, however, to transfer the high voltage necessary for the generation of a plasma from a high voltage generator to the device. The essential function of the cable is the safe transmission of the high voltage, the safe insulation to the outside (contact protection) and to the inside (dielectric strength). In addition, the cable must be flexible. The cable thus provides an electrical high-voltage connection between the device and the high-voltage generator, the cable comprising at least one HV conductor, an insulator and a ground line. For reasons of electrical safety and EMC, an additional shielding is preferably provided, which is either identical to the ground line or independently connected to the protective conductor (PE). The type of shielding depends primarily on the disturbances that occur. Particularly good shielding performance can be achieved by means of a double shielding (metallic or metallized foil and a screen braid). For the outer insulation of the high-voltage cable, a biocompatible, disinfectable material is preferred since, in practice, the cable is frequently fixed to the body of the patient by means of a patch. Furthermore, further electrical (control) lines, for example a data line for communication with a memory chip integrated in the device, can be provided. In addition or alternatively, a double shielding and/or ferrite cores for EMC improvement, gas line(s) for supplying working gases such as humidified air and/or noble gas(es) as well as special gas mixtures, or for discharging (suction lines) undesirable gas components, such as, for example, ozone can also be provided.

To improve the EMC characteristics, it may be necessary to integrate one or more further electronic components, such as coils, capacitors and filters, between the device according to the first aspect of the invention and the HV-cable. Furthermore, the above-mentioned measures for improving the electrical safety and the EMC can also be provided between the device and the HV-cable.

The connection of the cable to the device can optionally be fixed or via a plug-in system. The plug variant allows easy replacement of the cable for defects and/or for cleaning/disinfecting purposes. Furthermore, all possible cable lengths from 1 m to 20 m are provided.

Preferably, an embodiment provides that the cable has a clamping device, wherein the clamping device is displaceable between an open position and a closed position and in the closed position the device is electrically connected to the cable and in the open position the device is electrically disconnected from the cable.

Preferably, the cable and clamping device are designed as a (high-voltage) one-way product, wherein an invalidation of the one-time product is provided after the treatment, for example, if it is only to be used once for hygienic reasons.

In the plug of the cable, a grounding and high-voltage contacting is preferably arranged laterally offset side by side.

A third aspect of the invention relates to a generator unit for providing a high voltage for producing a cold atmospheric pressure plasma with a device according to the first aspect of the invention for the treatment of human and/or animal surfaces, the generator unit being configured to control the device.

The generator unit is a central control unit for the (plasma) device and serves primarily to provide the high voltage by means of a high voltage generator for the device. The generator unit comprises a high-voltage generator with a control unit and at least one connection for the (supply) cable of the (plasma) device, as well as a mains connection with mains switch (main switch) and possibly integrated network filter and a cooler for cooling the electronics. Optionally, a gas connection is provided with a gas flow controller and/or a compressor and/or a suction device. In addition, further control units, microcontrollers, boards, displays, in particular touchscreen displays, foil keypads, etc., are preferably provided for operating the generator unit.

In a suitable embodiment, it can be provided that the generator unit is additionally configured to read operating parameters for controlling the device automatically from or in an information carrier, in particular a chip, a label and/or another information-und storage medium in or on the device. Depending on the type of the connected device, in particular depending on the size and/or the specific treatment parameters, the corresponding operating parameters are then read from an information carrier and provided to the generator unit. These can then, for example, also be displayed on the display, in particular the touchscreen display, of the generator unit.

A fourth aspect of the invention relates to a system comprising a device according to the first aspect of the invention, a cable according to the second aspect of the invention, and a generator unit according to the third aspect of the invention.

Embodiments of the invention are described below with reference to the figures. These are not intended to represent the exemplary embodiments to scale, but rather the figures are designed in a schematic and/or slightly distorted form. The features disclosed in the description, in the figures and in the claims can be essential both individually and in any combination for the realization of the invention. Identical and/or similar features with the same or similar function, where appropriate, are provided with the same reference symbols. Further advantages, features and details of the invention can be gathered from the following description of the preferred exemplary embodiments as well as from the figures.

In detail.

Figure 1:
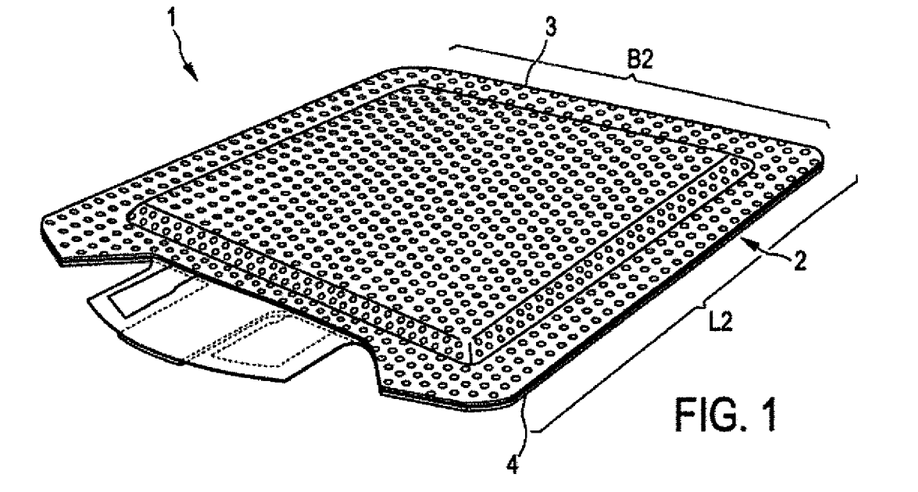
FIG. 1: shows a perspective, schematic representation of a device for producing a cold atmospheric pressure plasma for the treatment of surfaces.

FIG. 1 shows a perspective view of a device 1 for producing a cold atmospheric pressure plasma. The illustrated device 1, also called plasma patch, is a large-area plasma source for the treatment of human and/or animal surfaces, in particular for treating wounds and promoting the healing of wounds. The device makes use of a special, flexible electrode arrangement with two electrode layers, namely a high-voltage electrode and a ground electrode, for producing an extensive plasma by means of a dielectric layer between the two electrodes, wherein the device is configured to be flexibly placed on arbitrarily curved surfaces and thus suitable for the plasma treatment of diseased/damaged skin areas. In this case, the device 1 produces an extensive plasma on one side of the device, wherein the device is then placed with this side on the surface to be treated, in particular on a wound, so that the advantageous effects/properties of the plasma can take effect on the surface.

The device 1 comprises a flexible, extensive multilayer system 2 with a side 3 facing the surface to be treated and a side 4 facing away from the surface to be treated. The multilayer system 2 is thereby formed with several layers, which are described in detail in FIG. 2. The outer dimensions, in particular the dimensions of the multilayer system 2, have a length L2 and a width B2 between 5 cm to 25 cm, preferably 20 cm×20 cm. Without limiting the invention, however, other shapes, not only square shapes, can also be provided. Preferably, they then fit positively to the surface, for example, the face of a patient. Also provided are devices in the form of cuffs, pads, bed covers, bed sheets or the like.

Figure 2:
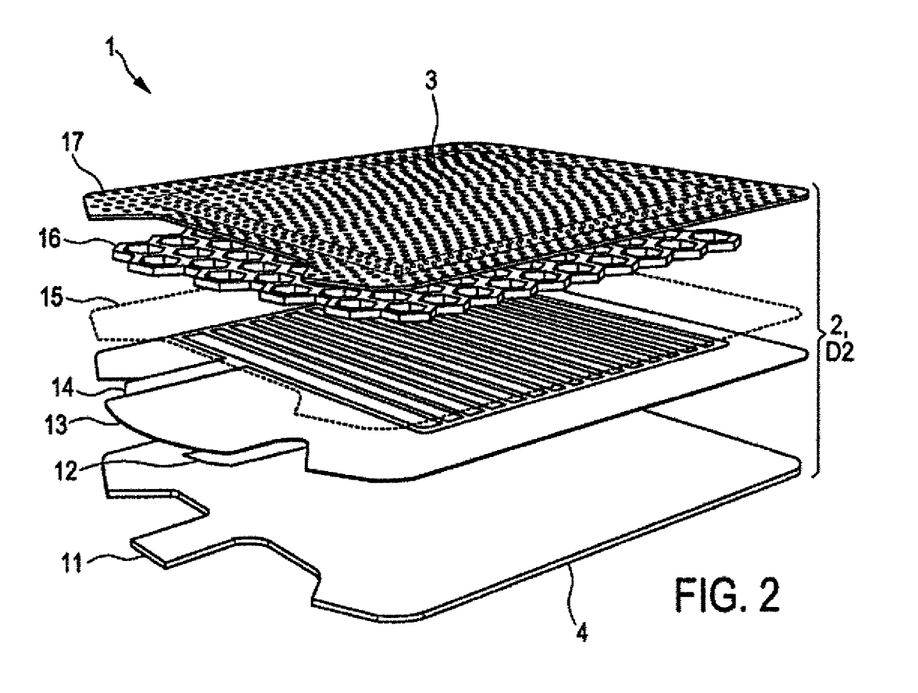
FIG. 2: shows an exploded view of the device shown in FIG. 1.

FIG. 2 shows an exploded view of the device 1 shown in FIG. 1, with a multilayer system 2. The multilayer system 2 comprises the following layers, namely (from below):
- a first insulating layer 11,
- a first electrode layer 12,
- a dielectric layer 13,
- a second electrode layer 14,
- a second insulating layer 15,
- a spacer layer 16, and
- a third insulating layer 17.

The first insulating layer 11 is arranged on the side 4 of the multilayer system 2 facing away from the surface to be treated and has a thickness of between 0.5 mm and 4 mm, preferably of 2 mm. The first insulating layer 11 is essentially for insulating the first electrode layer 12, which is preferably formed as a high-voltage layer, that is, an electrode layer to which a high voltage is applied.

The dielectric layer 13 is arranged between the first electrode layer 12 and the second electrode layer 14, the second electrode layer 14 preferably being designed as a ground electrode layer. The dielectric layer 13 essentially prevents a short circuit between the first and second electrode layer, in particular in the form of an electrical arc.

Furthermore, in a preferred embodiment, on the second electrode layer 14 a second insulating layer 15 is arranged that has a thickness of between 10 μm and 300 μm.

Above the second electrode layer 14 or the second insulating layer 15, that is to say on the side 3 of the multilayer system 2 facing the surface to be treated, the spacer layer 16 is then arranged, which ensures that sufficient gas volumes are provided so that a plasma can ignite.

Finally, a third insulating layer 17 is arranged on the side 3 of the multilayer system 2 facing the surface to be treated and above the spacer layer 16. The third insulating layer 17 has a thickness of between 100 μm and 300 μm, preferably of 200 μm, and is in direct contact with the surface to be treated. Preferably, the third insulating layer 17 is then formed with a skin- and/or wound-compatible material, preferably with antiseptic and/or atraumatic properties.

In the present case, as shown in FIG. 2, the second electrode layer 14 is formed with a plurality of recesses, in particular grid-like. Without restricting the invention, however, the recesses can also be designed in the form of holes, strips, meanders, honeycomb, circular and/or square.

Furthermore, the spacer layer 16 can also be formed in the form of a honeycomb, wherein the spacer layer 16 can also be realized by means of projections or webs without restriction of the invention. Possible materials for the spacer layer 16 are polymers, elastomers and/or silicones or the like. In principle, a large number of possible materials can be used, such as, for example, inorganic or organic materials, in particular natural and/or synthetic materials, such as thermoplastics, thermosets and/or elastomers. For further possible materials reference is also made, for example, to the book "Kunststoff-Taschenbuch" (28th edition) by Karl Oberbach and Hansjürgen Saechtling. In a preferred embodiment, the spacer layer is formed with projections and/or webs, which have a height between 0.5 mm and 10 mm.

Overall, the multilayer system shown in FIG. 2 has a thickness D2 of between 2 mm and 15 mm. Here, it is provided that the layers, which are in direct contact with the surface to be treated, are formed from a heat-resistant, biocompatible and chemically stable plastics.

Figure 3:
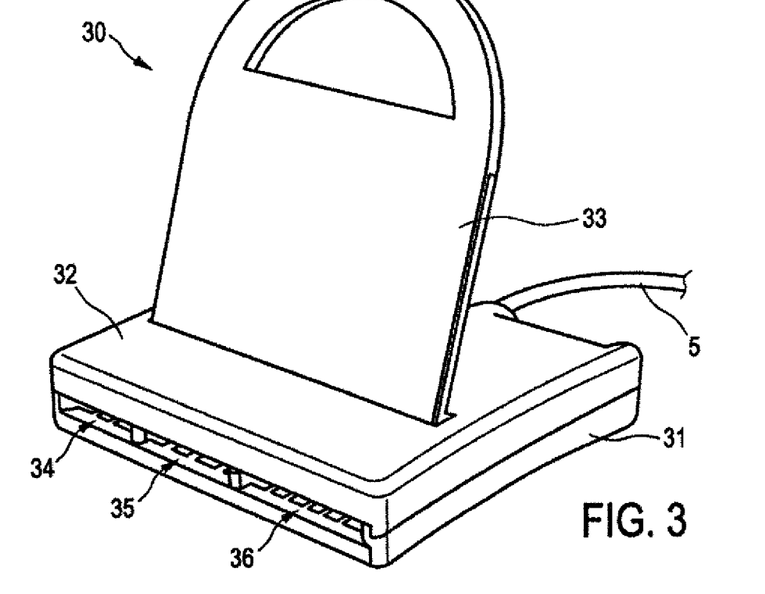
FIG. 3: shows a schematic representation of a preferred embodiment for a cable with a plug.

FIG. 3 shows a schematic representation of a preferred embodiment for a cable 5 with a plug 30. The essential task of the cable 5 is to transmit the high voltage necessary for the generation of a plasma from a high voltage generator (not shown) to the device, wherein the cable comprises at least one HV conductor, an insulator and a ground line (not shown). The connection of the cable to the device can optionally be fixed or via a plugging system, whereby the plug variant permits a simple replacement of the cable in the event of defects and/or for cleaning/disinfecting purposes. Furthermore, all possible cable lengths from 1 m to 20 m are provided.

The embodiment shown in FIG. 3 shows a cable with a possible plug, the plug 30 comprising a lower plug housing 31, an upper plug housing 32 and a clamping device 33. In addition, the plug 30 comprises a first terminal 34 for the first electrode of the device (not shown), a second terminal 36 for a second electrode of a device, and a further terminal 35 for control signals and or, for example, for reading operational parameters for the device that are for example stored on a chip in the device.

The illustrated clamping device 33 of the plug 30 is displaceable between a first open position and a second closed position. Here, the device (not shown) is electrically connected to the cable 5 in the closed position, and in the open position the device is then electrically disconnected from the cable 5.

Figure 4:
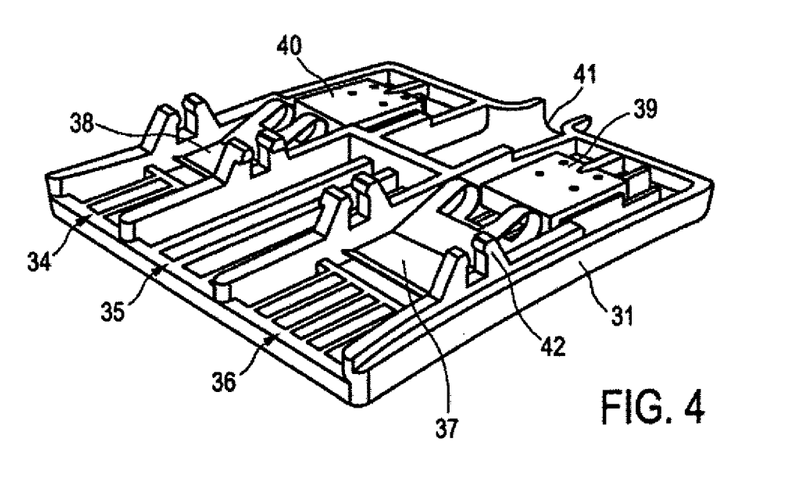
FIG. 4: a schematic representation of an embodiment for a plug housing.
Figure 5:
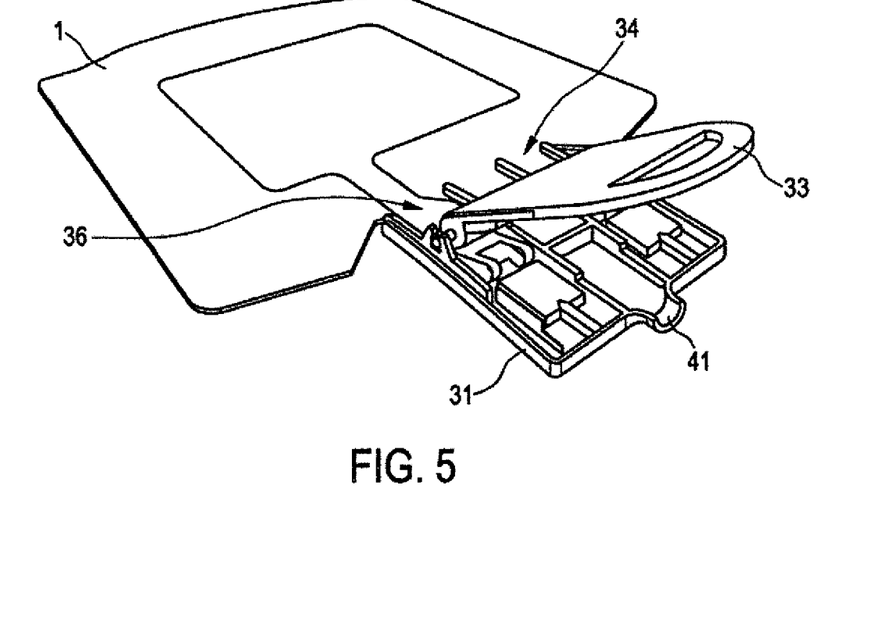
FIG. 5: a perspective, schematic representation of a device for treating surfaces and a plug.

FIG. 4 shows a possible embodiment of the interior of a plug 30, as is shown and described, for example, in FIG. 3. The connector, in particular the lower plug housing 31, comprises a first clamping tongue 37 and a second clamping tongue 38 each configured to connect the first or second electrode of the device (not shown) to a high voltage terminal 39 or a ground terminal 40 of the cable (not shown), wherein the cable is connected to the plug 30 via the cable connection 41. Furthermore, the plug 30 comprises at least one joint 42. By means of the joint 42, the clamping device 33 can be displaced from the open to the closed position and vice versa. Here, the clamping device interacts with the first clamping tongue 37 and the second clamping tongue such that, in the closed position, the first and/or second electrode of the device is electrically connected to the high-voltage connection 39 or the ground connection 40 of the cable. In the open position of the clamping device, the clamping tongues release the respective electrodes so that they are no longer electrically connected to the cable. Plugs and clamping devices are designed in such a way that they meet high voltage requirements.

FIG. 5 shows a perspective, schematic representation of a device 1 for treating surfaces, as is illustrated and described, for example, in FIG. 1, together with a plug 30, as is shown and described, for example, in FIGS. 3 and 4.

Figure 6:
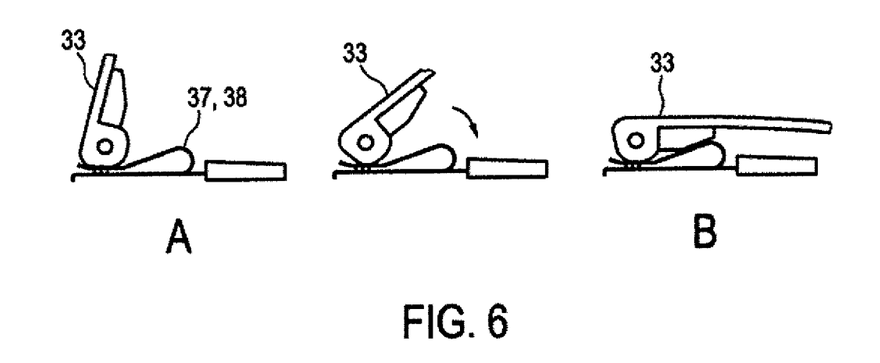
FIG. 6: a preferred embodiment for a clamping device for a plug.

FIG. 6 shows a preferred embodiment for a clamping device 33 for a plug (not shown) as is described in FIGS. 3 and 4. Schematically shown is the displacement movement of the clamping device 33 from the open position A to the closed position B, the arrow indicating the direction of movement of the clamping device during the displacement.

Figure 7:
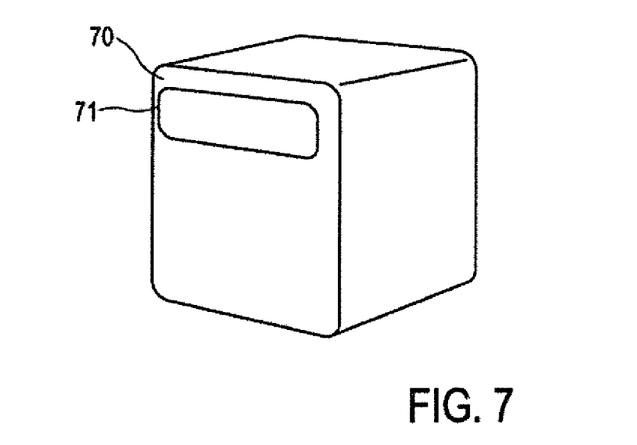
FIG. 7: a preferred embodiment for a generator.

FIG. 7 shows a preferred embodiment for a generator unit 70 for providing a high voltage for operating a device, as is illustrated and described, for example, in FIGS. 1 and 2. The generator unit 70 serves primarily to provide the high voltage by means of a high voltage generator for the device. For this purpose, the generator unit 70 comprises a high-voltage generator with a control unit and at least one connection for the (supply) cable of the (plasma) device and a mains connection with mains switch (not shown). Optionally, a gas connection is provided with a gas flow controller and/or a compressor and/or a filter and/or a suction device. Furthermore, a display 71, further control units, microcontrollers, boards, etc., are preferably provided for operating the generator unit.

The generator unit 70 is also configured to interact with a device, in particular to automatically read out the operating parameters of a particular device which are stored, for example, on a chip 80 (see also FIG. 8) in the device. Based on the read-out operating parameters, the generator unit can then be set automatically without having to set the parameter setting manually by a user at the generator unit. The operating parameters can then also be displayed on the display or screen 71 of the generator unit 70.

Figure 8:
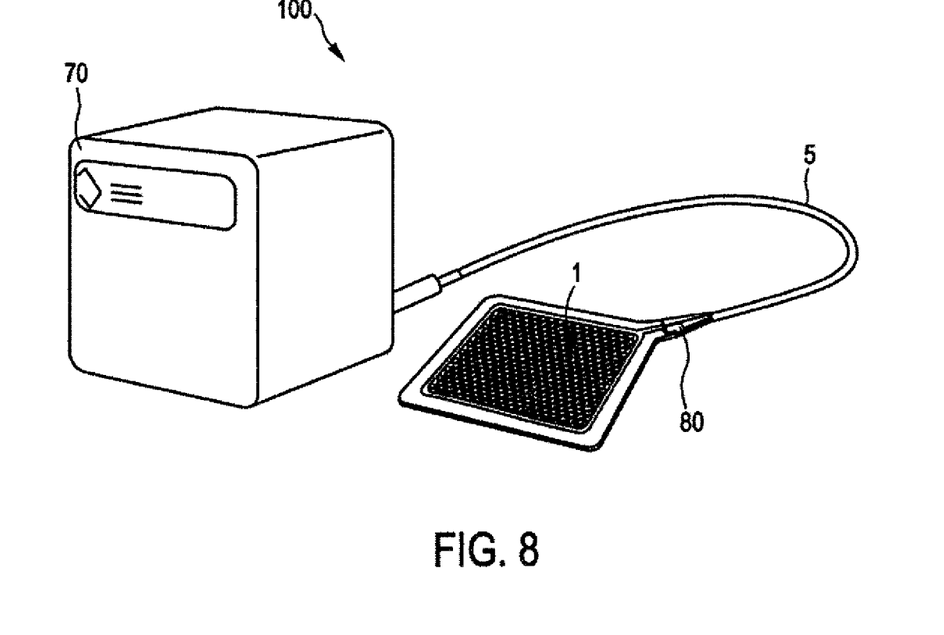
FIG. 8: a schematic representation for a preferred embodiment for a system with a device, a generator and a cable for connecting the device to the generator.

FIG. 8 shows a schematic representation of a preferred embodiment for a system 100 with a device, as shown, for example, in FIGS. 1 and 2, of a generator unit as described in FIG. 7, wherein the device and generator unit are controllably connected by means of a Cable 5.

Figure 9:
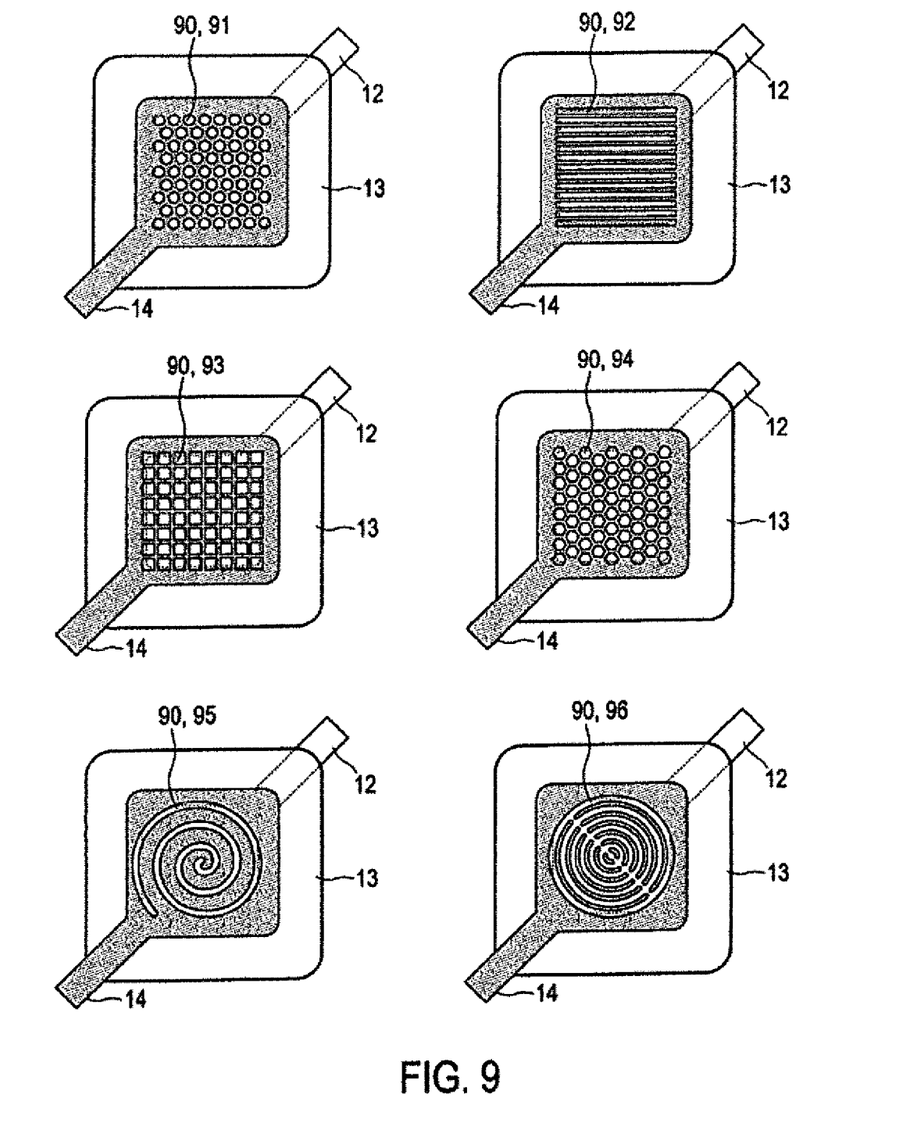
FIG. 9: preferred embodiments, in particular recesses in the electrode layer, for a device for treating surfaces.

FIG. 9 shows various embodiments, in particular recesses in the first and second electrode layer of a device for treating surfaces, as is shown and described, for example, in FIGS. 1 and 2. Various embodiments are shown, each having a first electrode 12, a second electrode 14, and a dielectric layer 13 between the first and second electrode 12, 14. Various shapes for recesses 90 in the second electrode 14 are shown, for example, hole-shaped 91, strip-shaped 92, meandering 95, honeycomb-shaped 94, circular 96 and/or square recesses 93. Without restricting the invention, it may also be provided that both the first and second electrodes 12, 14 are formed with recesses 90 in various shapes.

REFERENCE LIST 1 device
2 Multilayer system
3 Facing side of the device 1
4 Facing away side of device 1
5 Cable
11 First insulating layer
12 First electrode layer, in particular high-voltage electrode layer
13 Dielectric layer
14 Second electrode layer, in particular ground electrode layer
15 Second insulating layer
16 Spacer layer
17 Third insulating layer
30 Plug
31 Lower plug housing
32 Top plug housing
33 Clamping device
34 Connection for the second electrode layer 14
35 Additional Connection
36 Connection for the first electrode layer 12
37 First clamping tongue
38 Second clamping tongue
39 High voltage connection
40 Ground connection
41 Cable connection
42 Joint
70 Generator unit
71 Display
80 Information carriers
90 Recess in the first and/or second electrode layer
91 Hole-shaped recess
92 Strip-shaped recess
93 Square recess
94 Honeycomb-shaped recess
95 Meandering recess
96 Circular and/or semi-circular recess
100 System
A Open position of the clamping device 33
B Closed position of the clamping device 33
D2 Thickness of the multilayer system 2
L2 Length of the multilayer system 2
B2 Width of the multilayer system 2

The invention claimed is:

1. A device (1) for producing a cold atmospheric pressure plasma for the treatment of human and/or animal surfaces, comprising a flexible, extensive multilayer system (2) with a side (3) facing the surface to be treated and a side (4) facing away from the surface to be treated, the multilayer system (2) comprises the following layers:
   a first electrode layer (12) on the side (4) facing away from the surface to be treated of the multilayer system (2),
   a second electrode layer (14) on the side (3) facing the surface of the multilayer system (2), wherein the second electrode layer comprises a plurality of recesses (90) or is formed like a grid or meandering,
   a dielectric layer (13) arranged between the first electrode layer (12) and the second electrode layer (14),
   a first insulating layer (11) arranged adjacent to the first electrode layer (12) on the side (4) of the multilayer system (2) facing away from the surface to be treated,
   a flexible second insulating layer (15) arranged adjacent to the second electrode layer (14) on the side (3) of the multilayer system (2) facing the surface to be treated,
   a spacer layer (16) arranged adjacent to the flexible second insulating layer (15) on the side (3) facing the surface to be treated of the multilayer system (2), wherein the spacer layer (16) is configured to provide a sufficient gas volume so that a plasma can ignite,
   a third insulating layer (17) arranged adjacent to the spacer layer (16) on the side (3) of the multilayer system (2) facing the surface to be treated.

2. The device (1) according to claim 1, wherein the spacer layer (16) is formed with a textile fabric and with a thickness of 0.5 mm to 10 mm.

3. The device (1) according to claim 1, wherein the first insulating layer (11) has a thickness between 0.5 mm and 5 mm.

4. The device (1) according to claim 1, wherein the flexible second insulating layer (15) has a thickness between 10 μm to 300 μm.

5. The device (1) according to claim 1, characterized in that the third insulating layer (17) has a thickness between 50 μm to 300 μm.

6. The device (1) according to claim 1, wherein the first electrode layer (12) is formed continuously or with a plurality of recesses.

7. The device (1) according to claim 1, wherein the plurality of recesses (90) in the first and/or second electrode layer (12, 14) have a hole-shaped (91), strip-shaped (92), meandering (95), honeycomb-shaped (94), circular (96) and/or square (93) design.

8. The device (1) according to claim 1, wherein the spacer layer (16) and the dielectric layer (13) are separate layers or are made from a different material.

9. The device (1) according to claim 1, wherein the device (1) comprises an information carrier (80), on which at least one operating parameter for operating the device (1) is stored, wherein the information carrier (80) stores information on the kind of use of the device (1), whether the kind of use is single-use only or multiple use.

10. The device (1) according to claim 1, wherein the information carrier (80) is a barcode or QR-code.

11. The device (1) according to claim 1, wherein the flexible second insulating layer (15) is not integrally formed with the spacer layer (16).

12. The device (1) according to claim 1, wherein the second insulating layer is made from a different material than the spacer layer.

13. The device (1) according to claim 1, wherein the flexible second insulating layer (15) is not integrally formed with the dielectric layer (13).

14. The device (1) according to claim 1, wherein the flexible second insulating layer (15) is made from a different material than the dielectric layer (13).

15. The device (1) according to claim 1, wherein the spacer layer (16) has recesses in form of a honeycomb structure.

16. The device (1) according to claim 1, wherein the spacer layer (16) comprises a self-adhesive margin with which the device is attachable to a patient.

* * * * *